(12) United States Patent
Formica et al.

(10) Patent No.: US 8,978,648 B2
(45) Date of Patent: Mar. 17, 2015

(54) AIR DELIVERY CONDUIT

(75) Inventors: Justin John Formica, Voyager Point (AU); James Morrison, Thornleigh (AU)

(73) Assignee: ResMed Limited, Bella Vista (AU)

( * ) Notice: Subject to any disclaimer, the term of this patent is extended or adjusted under 35 U.S.C. 154(b) by 428 days.

(21) Appl. No.: 13/064,676

(22) Filed: Apr. 7, 2011

(65) Prior Publication Data

US 2011/0247619 A1 Oct. 13, 2011

(30) Foreign Application Priority Data

Apr. 7, 2010 (AU) ................. 2010901460

(51) Int. Cl.
| | |
|---|---|
| A61M 16/00 | (2006.01) |
| A62B 7/00 | (2006.01) |
| A62B 18/02 | (2006.01) |
| F16L 11/00 | (2006.01) |
| F16L 11/11 | (2006.01) |
| A61M 16/08 | (2006.01) |
| A61M 16/06 | (2006.01) |

(52) U.S. Cl.
CPC .......... *F16L 11/111* (2013.01); *A61M 16/0875* (2013.01); *A61M 16/0683* (2013.01)
USPC .................. 128/204.18; 128/205.25; 138/121

(58) Field of Classification Search
USPC .......... 138/121, 173, 177, 178, DIG. 11, 172, 138/174; 128/205.25, 204.18; 604/524–527
See application file for complete search history.

(56) References Cited

U.S. PATENT DOCUMENTS

| | | | |
|---|---|---|---|
| 1,596,754 A | 8/1926 | Moschelle | |
| 1,928,992 A | 10/1933 | Clark et al. | |
| 3,720,235 A | 3/1973 | Schrock | |
| 3,756,244 A | 9/1973 | Kinnear et al. | |
| 3,974,862 A | 8/1976 | Fuhrmann | |
| 4,131,399 A | 12/1978 | Calvet | |
| 4,257,422 A | 3/1981 | Duncan | |
| 4,420,016 A | 12/1983 | Nichols | |
| 4,867,485 A | 9/1989 | Seckel | |
| 4,878,491 A * | 11/1989 | McGilvray, III | 128/201.11 |
| 6,044,844 A | 4/2000 | Kwok et al. | |
| 6,056,018 A * | 5/2000 | Renaud | 138/121 |
| 6,102,078 A * | 8/2000 | Kramer, Jr. | 138/122 |
| 6,764,627 B2 | 7/2004 | D'Angelo | |
| 7,302,950 B2 | 12/2007 | Berthon-Jones et al. | |
| 7,322,379 B2 | 1/2008 | Evans | |
| 7,637,287 B2 | 12/2009 | Reinhard et al. | |
| 7,806,848 B2 * | 10/2010 | Henderson et al. | 604/8 |
| 7,931,023 B2 | 4/2011 | Berthon-Jones et al. | |
| 2002/0096173 A1 | 7/2002 | Berthon-Jones et al. | |
| 2007/0208300 A1* | 9/2007 | Pravong et al. | 604/96.01 |
| 2008/0036242 A1* | 2/2008 | Glance et al. | 296/187.09 |
| 2008/0060649 A1* | 3/2008 | Veliss et al. | 128/205.25 |
| 2009/0078259 A1* | 3/2009 | Kooij et al. | 128/205.25 |
| 2009/0217929 A1 | 9/2009 | Kwok et al. | |

* cited by examiner

*Primary Examiner* — Tan-Uyen (Jackie) T Ho
*Assistant Examiner* — Mark Wardas
(74) *Attorney, Agent, or Firm* — Nixon & Vanderhye P.C.

(57) ABSTRACT

An air delivery conduit includes a tube including a plurality of corrugations. The corrugations vary along a length of the tube to change flexibility and/or stretch characteristics of the tube in one or more specific zones.

40 Claims, 8 Drawing Sheets

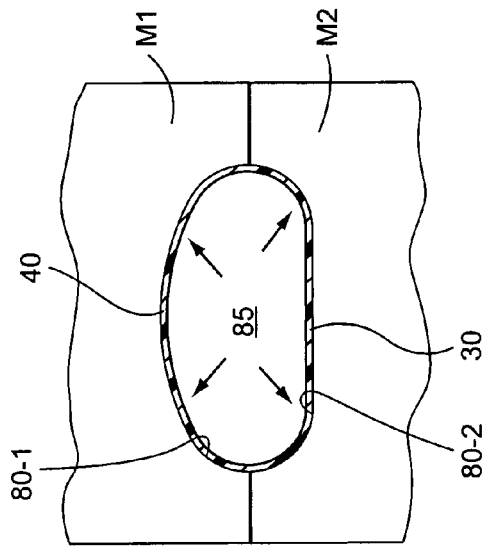
FIG. 15
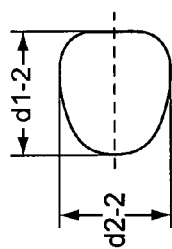
FIG. 14-2
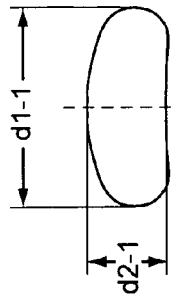
FIG. 14-1
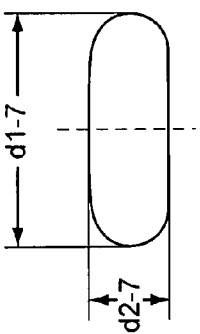
FIG. 14-4
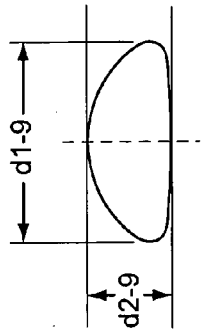
FIG. 14-7
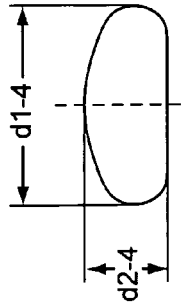
FIG. 14-3
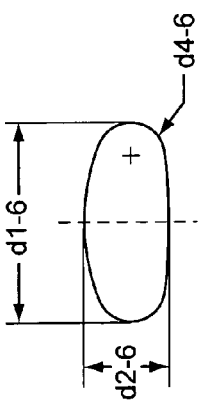
FIG. 14-5
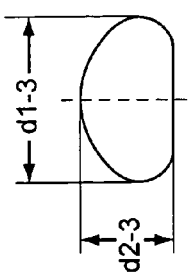
FIG. 14-6
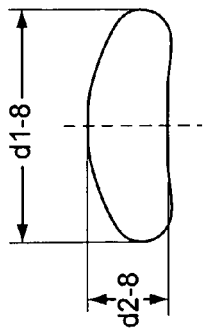
FIG. 14-8
FIG. 14-9

AIR DELIVERY CONDUIT

CROSS-REFERENCE TO APPLICATION

This application claims the benefit of Australian Provisional Application No. 2010901460, filed Apr. 7, 2010, which is incorporated herein by reference in its entirety.

FIELD OF TECHNOLOGY

The present technology relates to air delivery conduits used in Positive Airway Pressure (PAP) systems for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

PAP systems to deliver breathable gas to a patient typically include a positive airway pressure (PAP) device, an air or gas delivery conduit, and a patient interface. In use, the air delivery conduit delivers pressurized air or gas from the PAP device to the patient interface in contact with the patient's face.

The present technology provides improvements to known air delivery conduits to enhance comfort for the patient and/or lower manufacturing costs.

SUMMARY OF TECHNOLOGY

One aspect of the present technology relates to an air delivery conduit for use in the delivery of a supply of air or breathable gas to a patient, e.g., for treatment of respiratory disorders.

In an example, the air delivery conduit may have a generally D-shaped cross-section. In an example, a cross-section of the air delivery conduit may include a major axis and a minor axis.

In an example, the air delivery conduit may be constructed from polyethylene, polypropylene, EVA, or a blend of these materials.

In an example, the air delivery conduit has a first side adapted to be positioned against a face of a patient. In an example, the first side may be constructed and arranged to be substantially flat in cross-section. In an example, the first side may be constructed and arranged to be substantially parallel to a facial region of a patient in use. In an example, the first side may be constructed to be substantially free from corrugations. Preferably, the first side may be flexible. In an example, the first side may have a first stiffness.

In an example, the air delivery conduit includes a second side. In an example, the second side may includes one or more corrugations. In an example, the second side may be lengthwise extendible. Preferably, the second side may include a first region having a first pitch and second region having a second pitch. In an example, the conduit may vary in pitch between different regions. In an example, the second side may have a second stiffness that is less than the first stiffness.

In an example, the air delivery conduit may be constructed and arranged to flex while maintaining substantially patent. For example, the conduit may not include corrugations. In an example, the air delivery conduit may include structural reinforcement to reduce the tendency of the conduit to obstruct or collapse while bending.

In an example, the first side and the second side may be constructed from different materials, for example, a co-extrusion. In another example, the first side and the second side may be constructed from the same material, for example, a harder durometer and a softer durometer of the same material.

In an example, the air delivery conduit may be constructed and arranged to bend, flex and or be conformable to the shape of a patient's head in use.

Another aspect of the present technology relates to a method of manufacturing an air delivery conduit with an asymmetrical cross-sectional profile. In an example, the method includes an extrusion step followed by a blow-molding or vacuum forming step in one or more tools. In an example, a tool creates a corrugation on one side of an extruded tube, while creating a flat profile on another side of the extruded tube.

An advantage of an air delivery conduit or tube in accordance with one form of the present technology is that it is more comfortable for a patient compared to prior art designs. Another advantage of the present technology is that it may be constructed using a lower cost manufacturing process.

Another aspect of the present technology relates to an air delivery conduit including a tube including a plurality of corrugations, wherein the corrugations vary along a length of the tube to change flexibility and/or stretch characteristics of the tube in one or more specific zones.

Another aspect of the present technology relates to an air delivery conduit including a tube including a plurality of corrugations, wherein corrugations in a first zone of the tube have a first corrugation characteristic and corrugations in a second zone of the tube have a second corrugation characteristic that is different than the first corrugation characteristic.

Another aspect of the present technology relates to an air delivery conduit including a tube including a plurality of corrugations. A portion of the tube that includes the corrugations is asymmetric about at least one axis.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 14-1 to 14-9 show cross-sections of tubing according to alternative examples of the present technology; and FIG. 15 is a schematic view of a mold for manufacturing an air delivery conduit according to an example of the present technology.

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

One or more examples may include exemplary dimensions. Although specific dimensions and ranges may be provided, it is to be understood that these dimensions and ranges are merely exemplary and other dimensions and ranges are possible depending on application. For example, ranges that vary from those provided +/−10% may be suitable for particular applications.

PAP System

A PAP system (e.g., CPAP system) typically includes a PAP device (including a blower for generating air at positive pressure), an air delivery conduit (also referred to as a tube or tubing), and a patient interface adapted to form a seal with the patient's face. In use, the PAP device generates a supply of pressurized air (e.g., 2-30 cm $H_2O$) that is delivered to the patient interface via the air delivery conduit. The patient interface or mask may have suitable configurations as is known in the art, e.g., full-face mask, nasal mask, oro-nasal mask, mouth mask, nasal prongs, nozzles, cradle, etc. Also, headgear may be utilized to comfortably support the patient interface in a desired position on the patient's face.

Air Delivery Conduit

FIGS. 1-8 illustrate an air delivery conduit 10 according to an example of the present technology. In this example, the air delivery conduit is in the form of a non-heated tube including a tube 15, a first cuff or connector 20(1) provided to one end (i.e., a first end) of the tube, and a second cuff or connector 20(2) provided to the opposite end (i.e., a second end) of the tube. However, it should be appreciated that the conduit may be adapted for use as a heated tube.

In this example, the air delivery conduit is structured to be worn on the patient's head in use. For example, one or more of the air delivery conduits may be communicated with a patient interface to deliver breathable gas to the patient interface.

Figure 10:
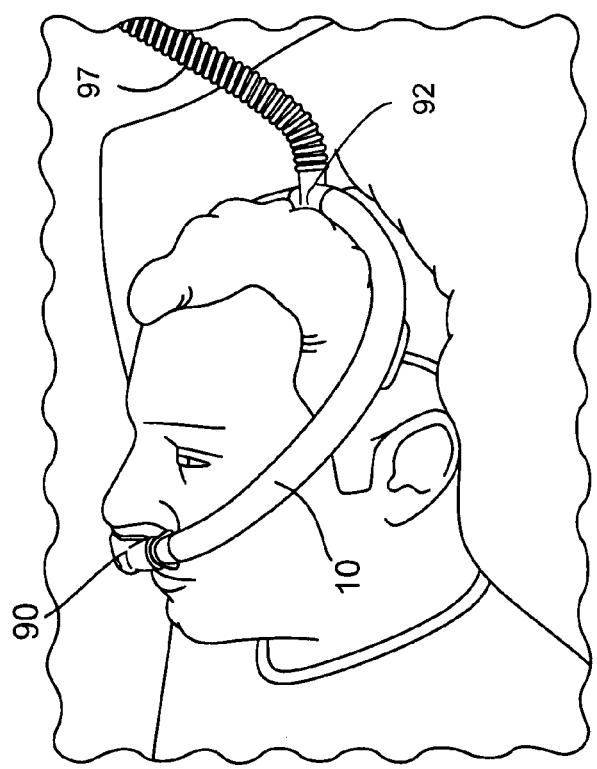
FIG. 10 is a perspective view showing the arrangement of FIG. 9.
Figure 9:
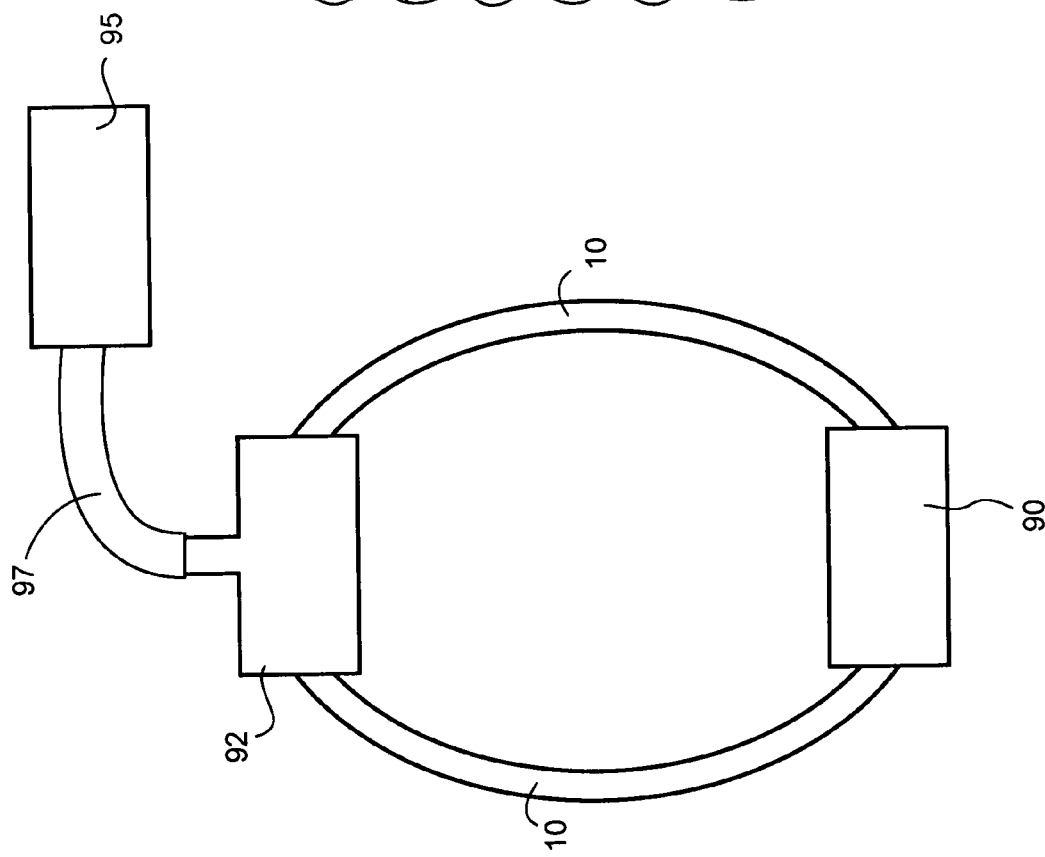
FIG. 9 is a schematic view showing air delivery conduits communicated with a patient interface and PAP device according to an example of the present technology.

In one example, a pair of air delivery conduits may be communicated with the patient interface. In an example, as shown in FIGS. 9 and 10, a first cuff of each conduit 10 may be adapted to engage a respective end or inlet of the patient interface 90 (e.g., nasal prong arrangement) and the second cuff may be adapted to engage a respective end of a manifold 92 communicated with the outlet of the PAP device 95 via another air delivery conduit 97.

Figure 12:
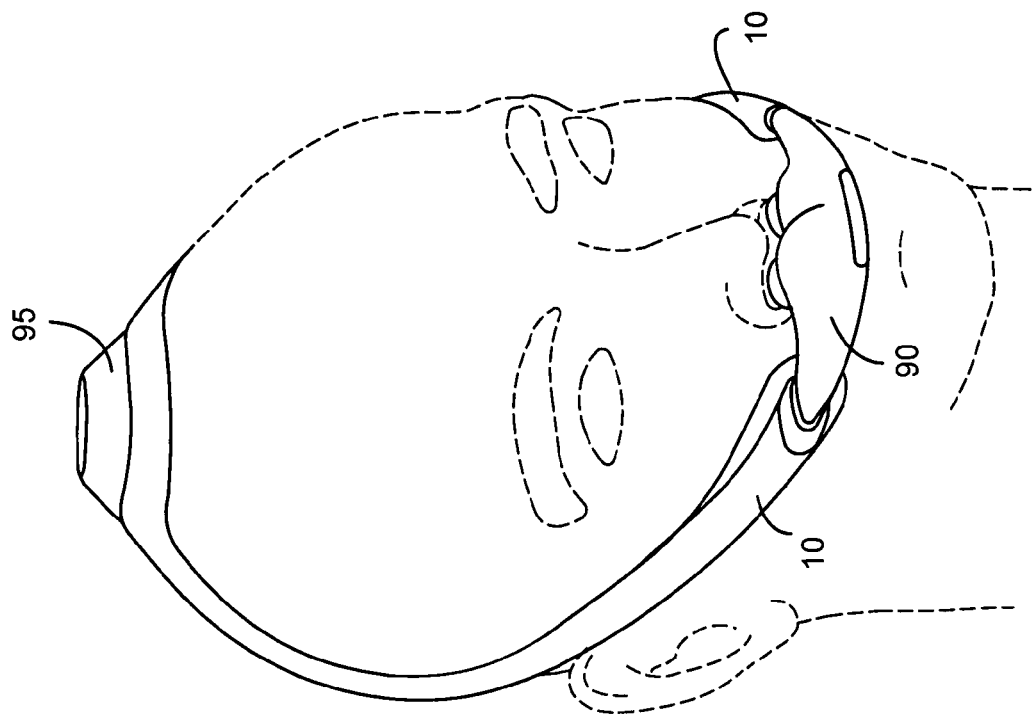
FIG. 12 is a perspective view showing the arrangement of FIG. 11.
Figure 11:
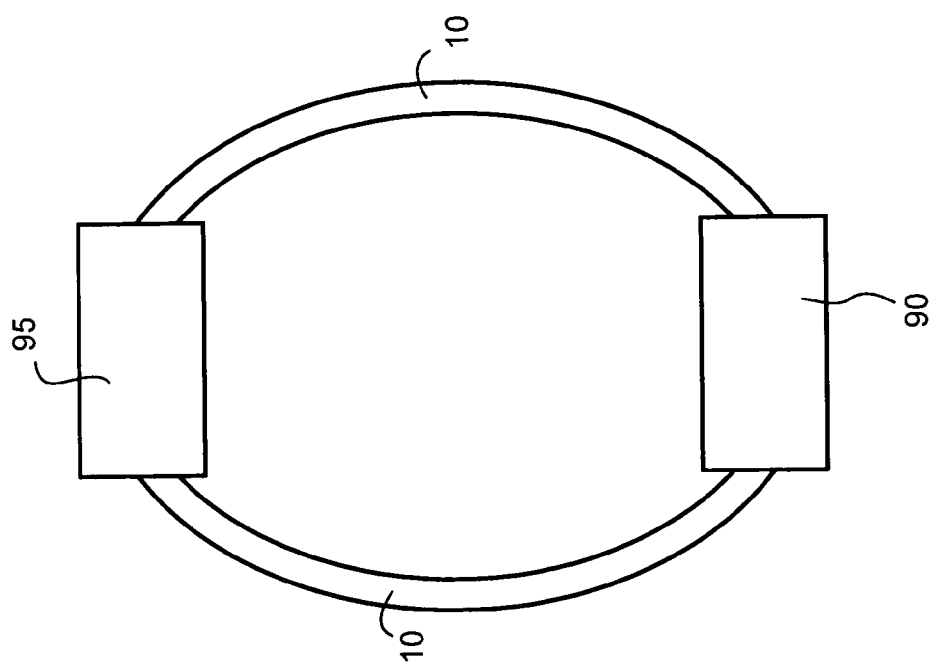
FIG. 11 is a schematic view showing air delivery conduits communicated with a patient interface and PAP device according to another example of the present technology.

In another example, as shown in FIGS. 11 and 12, each conduit 10 may be directly connected to the PAP device 95, e.g., positioned on the patient's head in use. For example, the first cuff of each conduit 10 may be adapted to engage a respective end or inlet of the patient interface 90 and the second cuff may be adapted to engage a respective outlet of the PAP device 95.

In each example, each conduit is adapted to extend from adjacent to or under the patient's nose, over the patient's cheeks, between the patient's eye and ear, and terminate at the crown of the patient's head.

It should be appreciated that the air delivery conduit may be provided along the air delivery path in other suitable manners. For example, the air delivery conduit may be structured to extend from the inlet of the patient interface, over the nose and between the patient's eyes, and to a manifold or PAP device positioned adjacent the crown of the patient's head. It may also be possible to position the conduit along the patient's cheeks and under their ears to the back of their head. It is also possible for the conduit to be asymmetrical on the patient's head, e.g., extending from only one side of the patient interface.

Also, while the air delivery is described as being implemented into a CPAP system of the type described above, it may be implemented into other tubing arrangements for conveying gas or liquid. That is, the CPAP system is merely exemplary, and aspects of the present technology may be incorporated into other suitable arrangements.

Cross-Section Configuration

Figure 8:
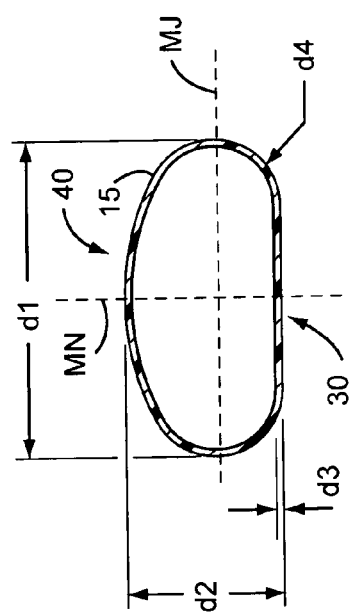
FIG. 8 is a cross-sectional view through line 8-8 of FIG. 5.

In the illustrated example, as best shown in FIG. 8, the tube 15 has a generally D-shaped cross-section including a first or inwardly facing surface 30 and a second or outwardly facing surface 40. The inwardly facing surface 30 (also referred to as a hidden or patient contacting side) is adapted to contact the patient's face in use, and the outwardly facing surface 40 (also referred to as a non-patient contacting side) is adapted to face away from the patient's face in use. The non-patient contacting side is the side that is viewable or exposed to an observer in use.

Figure 3:
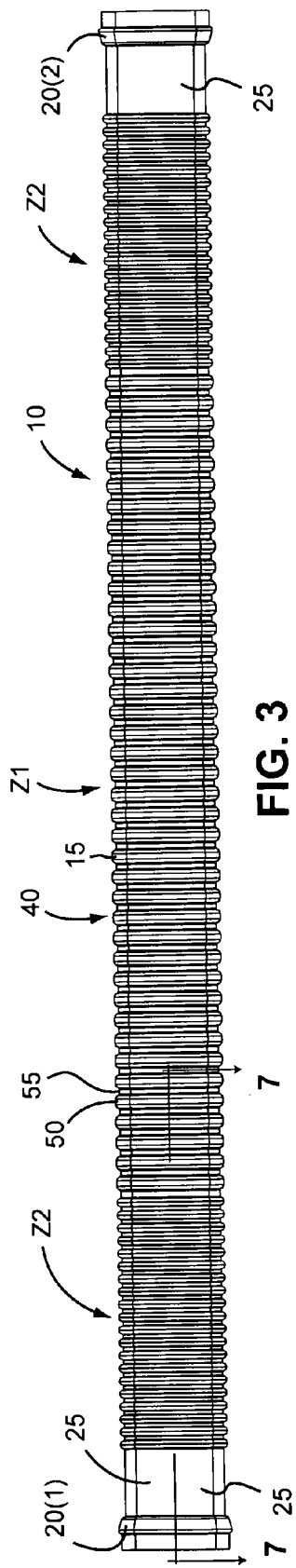
FIG. 3 is a top view of the air delivery conduit of FIG. 1.
Figure 5:
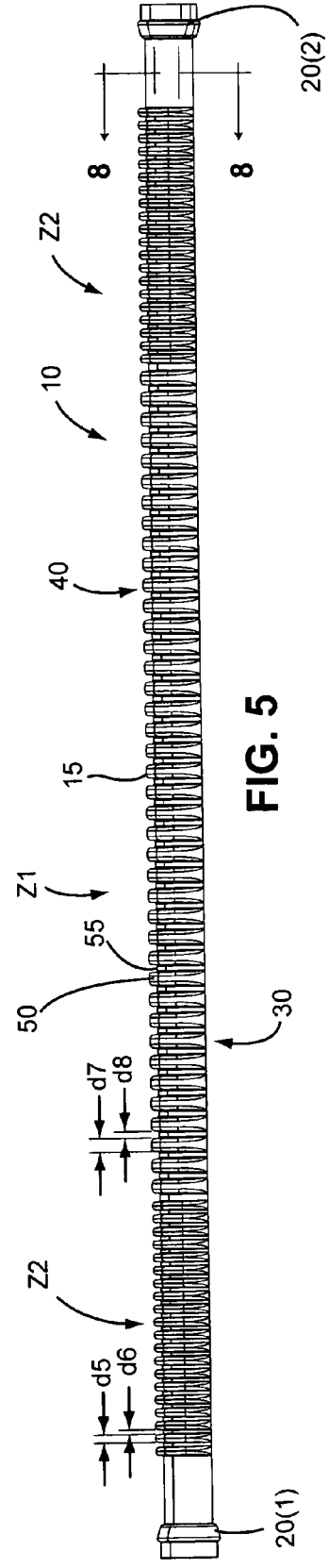
FIG. 5 is a side view of the air delivery conduit of FIG. 1.

As shown in FIG. 8, the generally D-shaped tube includes a major axis MJ and a minor axis MN. FIG. 3 shows the extent of the major axis (i.e., by viewing in a direction perpendicular to the major axis), and FIG. 5 shows the extent of the minor axis (i.e., by viewing in a direction perpendicular to the minor axis). In an example, as shown in FIG. 8, d1 along the major axis is about 15-20 mm, e.g., 18 mm, and d2 along the minor axis is about 5-10 mm, e.g., 8.3 mm. In an example, a ratio of the major axis to the minor axis MJ/MN may be about 1 to 4, e.g., about 1.5 to 3.5, about 2 to 3, about 1.7 to 2.7, about 2 to 2.5, about 2.2.

As shown in FIG. 8, the tube may have a relatively thin wall thickness d3 of about 0.4 mm. However, the tube may have a wall thickness in the range of about 0.3 mm to 0.5 mm.

Figure 1:
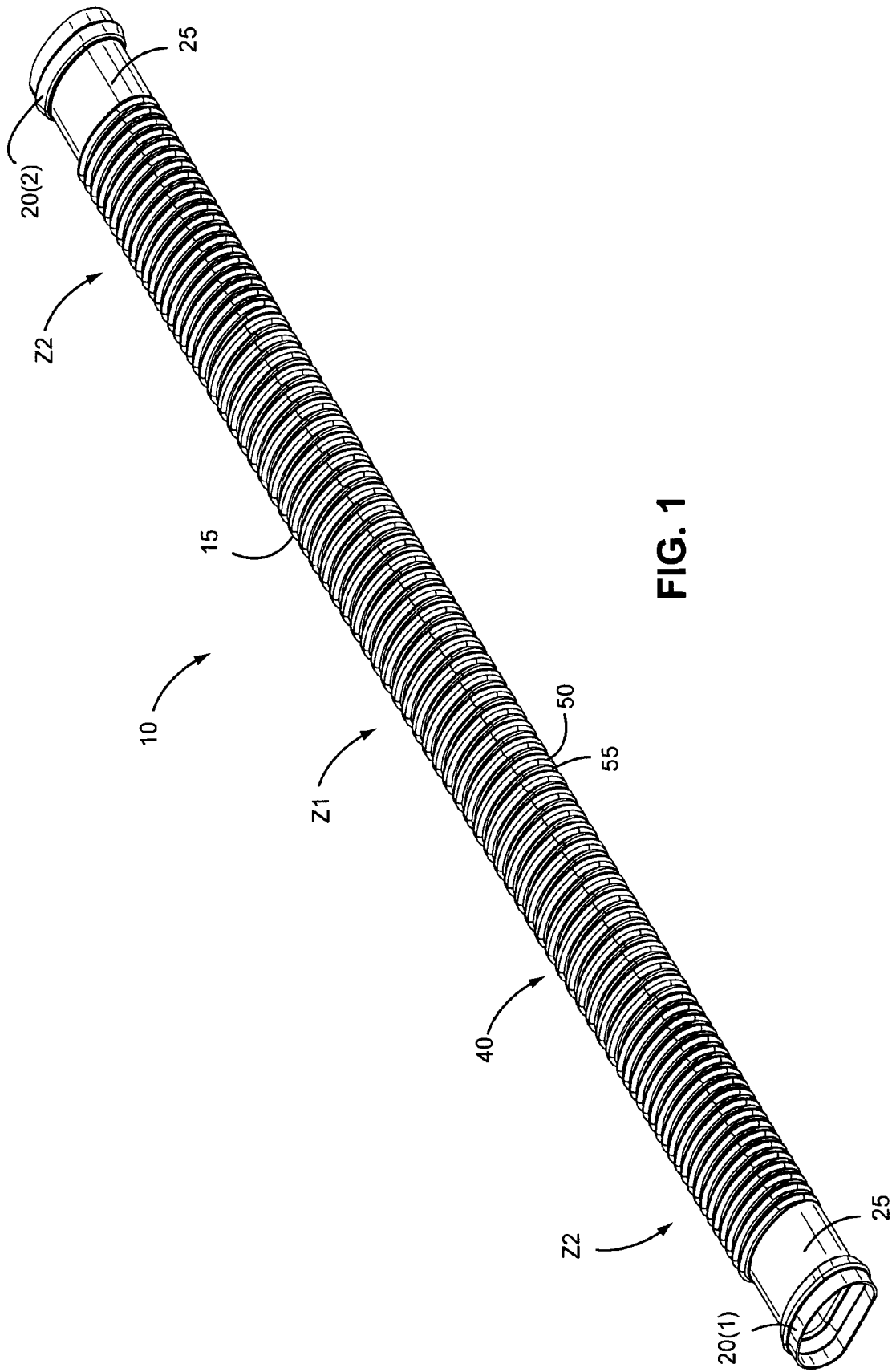
FIG. 1 is a top perspective view of an air delivery conduit according to an example of the present technology.

In the example, the tube is asymmetric about at least one axis, i.e., the major axis of the tube as shown in FIG. 8. As described below, FIGS. 14-1 to 14-9 show alternative examples of tubes that are asymmetric about at least one axis.

The cross-sectional configuration is substantially constant along the length of the tube, e.g., tube size may vary due to corrugations discussed below. However, the generally D-shaped cross-section may vary along its length.

Also, it is possible for the wall thickness of the tube to vary around the perimeter, e.g., less thick on patient contacting side so that hardness is low, i.e., more comfortable, and thicker on non-patient contacting side to prevent kinking or occlusion. Alternatively, the tube may be thicker on the patient contacting side with low hardness material, e.g., 5

Shore A silicone, so that is it soft and gel-like on the patient's skin, and thinner on the non-patient contacting side to permit greater flex.

Patient Contacting Side

As best shown in FIGS. 2, 4, 5, 7, and 8, the inwardly facing surface 30 or patient contacting side is relatively flat or smooth, i.e., patient contacting side substantially flat in cross-section. The inwardly facing surface is adapted to be positioned against the patient's face in use, e.g., adapted to sit substantially flush or parallel against the patient's face in use. Such flat arrangement increases comfort for the patient in use and reduces facial marking.

In an alternative example, the inwardly facing surface may include a slight contour or curvature, e.g., to more closely follow a curvature of the patient's face in use.

In an example, the patient contacting side is substantially free from corrugations, i.e., in contrast to the non-patient contacting side which includes multiple corrugations as described below.

The patient contacting side may be flexible. In an example, the patient contacting side may have a first stiffness. For example, the patient contacting side may be made from a material having a Shore hardness of about 30-70 Shore A, e.g., preferably 30-50 Shore A. In an alternative example, the patient contacting side may have a relatively low hardness, e.g., as low as 5 Shore A, with additional reinforcement, e.g., one or more reinforcing ribs.

Also, the patient contacting side may be frosted to reduce friction and also enhance comfort and breathability. Alternatively, the patient contacting side may be grippy or sticky to ensure that the tube is in a stable position, e.g., made with a low durometer material that is tacky, e.g., 7 Shore A TPE, silicone. Also, one or more gripping members may be molded or otherwise provided to the patient contacting side, e.g., small dots made from a tacky material.

Non-Patient Contacting Side

As best shown in FIG. 8, the outwardly facing surface 40 or non-patient contacting side has a smooth contour. In an example, as shown in FIG. 8, the radius of curvature at d4 may be about 2-5 mm, e.g., 3.5 mm.

FIGS. 14-1 to 14-9 show cross-sections of tubing according to alternative examples of the present technology. In FIG. 14-1, d1-1 is about 24 mm and d2-1 is about 9.5 mm. The tube of FIG. 14-1 includes a cross-sectional area of about 196.35 mm$^2$, a perimeter of the cross-section of about 57.65 mm, and a hydraulic diameter of about 13.62 mm. In an example, a ratio of the major axis to the minor axis d1-1/d2-1 may be about 2-3, e.g., about 2.5.

Figure 2:
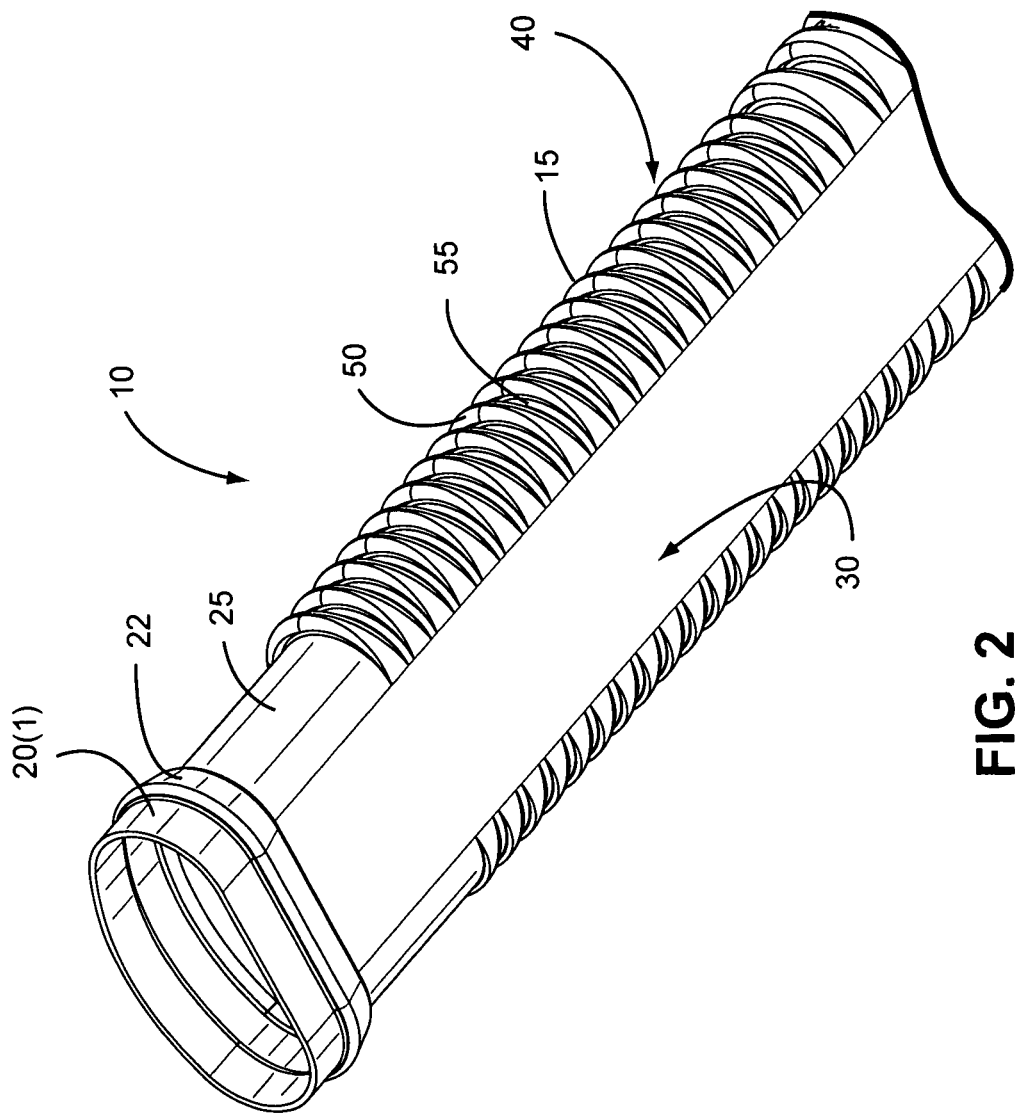
FIG. 2 is a bottom perspective view of a portion of the air delivery conduit of FIG. 1.

In FIG. 14-2, d1-2 is about 15 mm and d2-2 is about 13 mm. The tube of FIG. 14-2 includes a cross-sectional area of about 161.86 mm$^2$, a perimeter of the cross-section of about 46.09 mm, and a hydraulic diameter of about 14.05 mm. In an example, a ratio of the major axis to the minor axis d1-2/d2-2 may be about 1-2, e.g., about 1.2.

In FIG. 14-3, d1-3 is about 20 mm and d2-3 is about 11 mm. The tube of FIG. 14-3 includes a cross-sectional area of about 179.06 mm$^2$, a perimeter of the cross-section of about 51.04 mm, and a hydraulic diameter of about 14.03 mm. In an example, a ratio of the major axis to the minor axis d1-3/d2-3 may be about 1-2, e.g., about 1.8.

Figure 4:
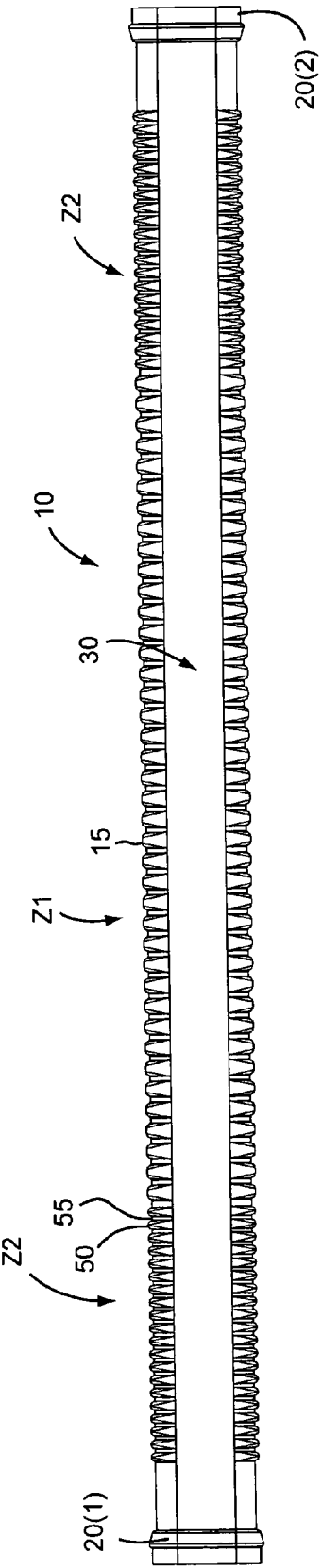
FIG. 4 is a bottom view of the air delivery conduit of FIG. 1.

In FIG. 14-4, d1-4 is about 24 mm and d2-4 is about 10 mm. The tube of FIG. 14-4 includes a cross-sectional area of about 202.50 mm$^2$, a perimeter of the cross-section of about 57.79 mm, and a hydraulic diameter of about 14.02 mm. In an example, a ratio of the major axis to the minor axis d1-4/d2-4 may be about 2-3, e.g., about 2.4.

In FIG. 14-5, d1-5 is about 20 mm, d2-5 is about 11.5 mm, and the radius of curvature at d4-5 of about 4 mm. The tube of FIG. 14-5 includes a cross-sectional area of about 183.29 mm$^2$, a perimeter of the cross-section of about 51.10 mm, and a hydraulic diameter of about 14.35 mm. In an example, a ratio of the major axis to the minor axis d1-5/d2-5 may be about 1-2, e.g., about 1.7.

Figure 6:
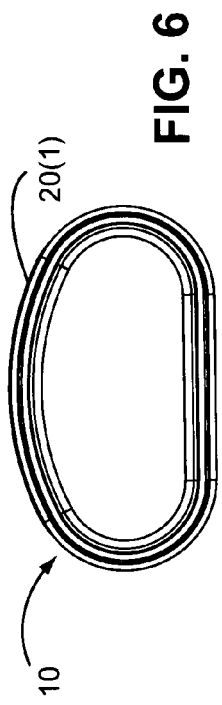
FIG. 6 is an end view of the air delivery conduit of FIG. 1.

In FIG. 14-6, d1-6 is about 24 mm, d2-6 is about 10 mm, and the radius of curvature at d4-6 of about 4 mm. The tube of FIG. 14-6 includes a cross-sectional area of about 201.37 mm$^2$, a perimeter of the cross-section of about 57.55 mm, and a hydraulic diameter of about 14.00 mm. In an example, a ratio of the major axis to the minor axis d1-6/d2-6 may be about 2-3, e.g., about 2.4.

Figure 7:
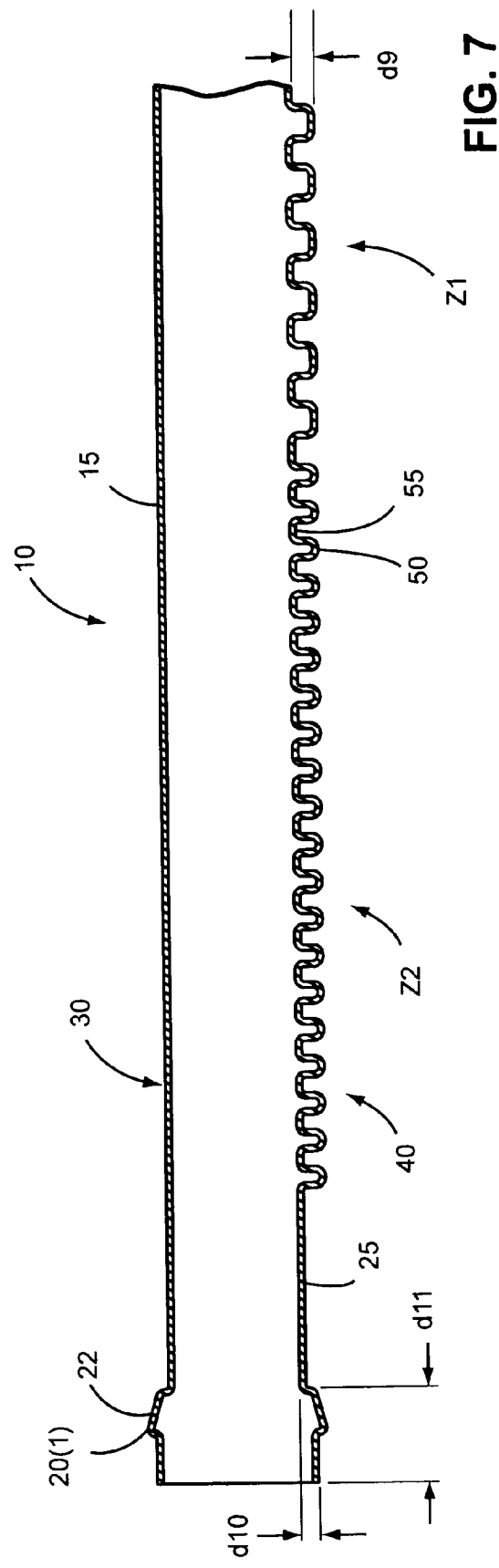
FIG. 7 is a cross-sectional view through line 7-7 of FIG. 3.

In FIG. 14-7, d1-7 is about 28 mm and d2-7 is about 9.5 mm. The tube of FIG. 14-7 includes a cross-sectional area of about 241.11 mm$^2$, a perimeter of the cross-section of about 66.31 mm, and a hydraulic diameter of about 14.54 mm. In an example, a ratio of the major axis to the minor axis d1-7/d2-7 may be about 2.5 to 3.5, e.g., about 3.

In FIG. 14-8, d1-8 is about 28 mm and d2-8 is about 9.5 mm. The tube of FIG. 14-8 includes a cross-sectional area of about 225.02 mm$^2$, a perimeter of the cross-section of about 65.10 mm, and a hydraulic diameter of about 13.83 mm. In an example, a ratio of the major axis to the minor axis d1-8/d2-8 may be about 2.5 to 3.5, e.g., about 3.

In FIG. 14-9, d1-9 is about 24 mm and d2-9 is about 10 mm. The tube of FIG. 14-9 includes a cross-sectional area of about 184.53 mm$^2$, a perimeter of the cross-section of about 56.42 mm, and a hydraulic diameter of about 13.08 mm. In an example, a ratio of the major axis to the minor axis d1-9/d2-9 may be about 2-3, e.g., about 2.4.

In an example, a hydraulic diameter of about 15 mm may be preferred, e.g., optimized for impedance. However, it should be appreciated that tubes with a smaller hydraulic diameter are possible. In such tubing, means may be provided to reduce impedance, e.g., such as an active valve. If the hydraulic diameter is smaller, the perimeter and area may also reduce, but the general shape of the cross section may be the same.

The non-patient contacting side includes one or more corrugations, folds, grooves, and/or ridges. In the illustrated example, the non-patient contacting side includes a plurality of corrugations, and the corrugations vary along the length of the tube, e.g., to change the flexibility and/or stretch characteristics of the tube in one or more specific zones.

The corrugations are provided along the curved or contoured portion of the tube (non-patient contacting side), while no corrugations are provided are provided along the flat portion of the tube (patient contacting side). Thus, corrugations are only provided along a selected circumference of the tube, i.e., portion of tube circumference is corrugated and remaining portion of tube circumference is non-corrugated.

The corrugations are in the form of flexible ribbing that provide a series of parallel ridges/peaks 50 and grooves/valleys 55. The ridges 50 provide spaced-apart and parallel ring-like annular members along a length of the tube. That is, the ridges are generally straight, e.g., ridges extend generally perpendicular to a longitudinal axis of the tube. However, it should be appreciated that angled or spiral corrugations are possible.

As best shown in FIGS. 3 and 5, corrugations in a central zone or section Z1 of the tube have a first corrugation characteristic, and corrugations in end zones or sections Z2 on opposing sides of the central zone Z1 have a second corrugation characteristic that is different from the first corrugation characteristic. For example, corrugations in the end zones Z2 include ridges 50 with a smaller width and smaller spacing (or pitch) between adjacent ridges (i.e., grooves 55 with a smaller width) than corrugations in the central zone Z1.

In an example, as shown in FIG. 5, the width d5 of the ridge 50 in each end zone Z2 is about 1.25-1.75 mm, e.g., 1.5 mm, and the pitch or width d6 of the groove 55 in each end zone Z2 is about 0.75-1.25 mm, e.g., 1.0 mm. In contrast, the width d7 of the ridge 50 in the central zone Z1 is about 2-3 mm, e.g., 2.5 mm, and the pitch or width d8 of the groove 55 in the central zone Z1 is about 1-2 mm, e.g., 1.5 mm. As shown in FIG. 7, the height d9 of the ridges 50 in the central and end zones Z1, Z2 are substantially the same, e.g., about 1-2 mm, e.g., 1.5 mm.

Figure 13:
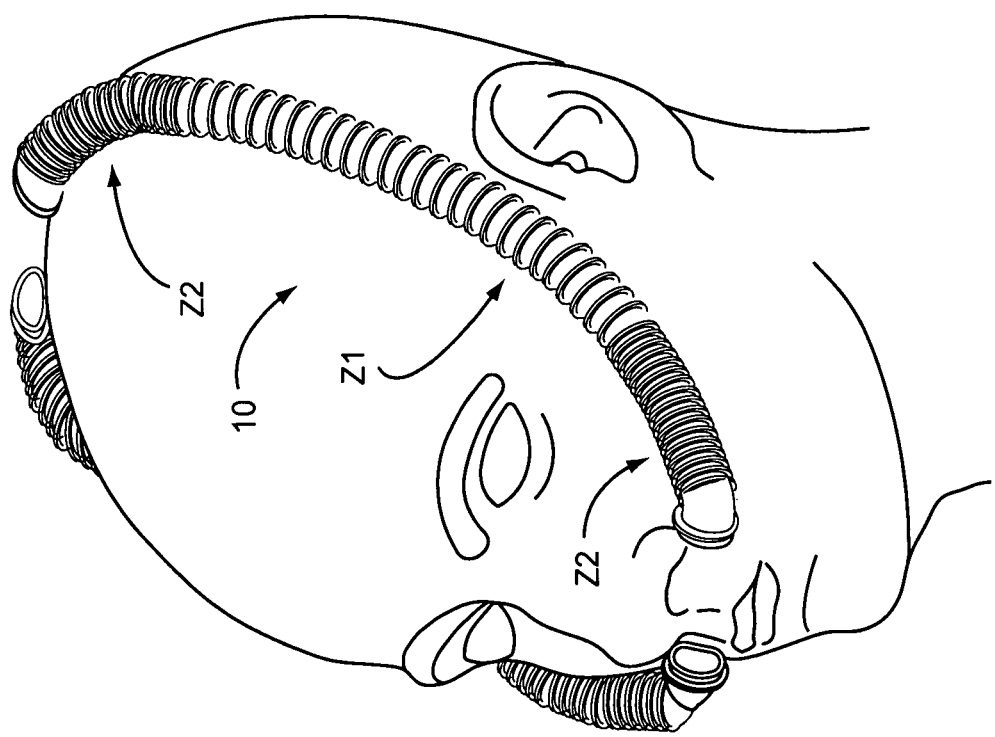
FIG. 13 is a perspective view showing air delivery conduits extending along the patient's head in use according to an example of the present technology.

The corrugations add rigidity and strength to the tube, with the corrugation characteristics selected to vary such rigidity and strength in different zones. In the illustrated example, the corrugations are smaller and closer together (smaller pitch) in the end zones Z2 which make the tube more flexible than the central zone Z1 in which the corrugations are larger and spaced farter apart (larger pitch). In use, as shown in FIG. 13, the less flexible central zone Z1 is adapted to extend along the cheek region of the patient's face. The more flexible end zones Z2 are adapted to extend adjacent to or under the patient's nose and near the top of the patient's head which allow more flexibility to adapt to typically more curved regions of the patient's head. However, it should be appreciated that the corrugations may vary in other suitable manners along the tube, e.g., corrugations constant, or vary in two, three, or more zones of the tube.

The corrugations also allow lengthwise extension of the tube, e.g., to allow lengthwise adjustment and/or flexibility of the tube. In an example, the corrugations may allow lengthwise extension in the range of about 60-100 mm.

In an example, the non-patient contacting side may have a second stiffness, which may be less than the first stiffness of the patient contacting side. For example, the non-patient contacting side may be made from a material having a Shore hardness of about 30-70 Shore A, e.g., preferably 50-70 Shore A. As noted above, the patient contacting side is preferably in the range of about 30-50 Shore A.

Also, it is possible for the tube to have alternative flexing means that are not corrugations, e.g., tube may be made from a material having alternative hardnesses or thicknesses along its length to increase flexibility in some regions more than others, e.g., high flexing regions made from 1 mm thick 30 Shore A silicone, and low flexing regions made from 5 mm thick 70 Shore A silicone, i.e., thickness and hardness of materials may be modified to achieve a similar affect.

Flexibility

In an example, the air delivery conduit may be constructed and arranged to bend, flex and/or be conformable to the shape of a patient's head in use. As described above, the conduit includes corrugations which may vary in different zones of the tube to vary flexibility.

In an example, the air delivery conduit may be constructed and arranged to flex while maintaining substantially patent. In an example, the air delivery conduit may include structural reinforcement (e.g., one or more internal ribs) to reduce the tendency of the conduit to obstruct or collapse while bending.

Cuff

As noted above, each end of the air delivery conduit includes a cuff 20(1), 20(2) structured to attach the conduit to the patient interface, PAP device, etc. In the illustrated example, each cuff 20(1), 20(2) is similar to one another. However, it should be appreciated that the cuffs may be different from one another. In an alternative example, the cuffs may include sensors or electronics/wiring associated with heating for heated tubes.

Each cuff includes a larger width or diameter than the tube, e.g., for alignment and engagement with a respective tubular connector of the patient interface, PAP device, etc. In an example, as shown in FIG. 7, the dimension d10 is about 0.5-1.0 mm, e.g., 0.80 mm.

Also, as best shown in FIGS. 2 and 7, each cuff includes an annular protrusion 22 to retain and/or seal with a respective tubular connector of the patient interface, PAP device, etc. As illustrated, the protrusion tapers along its length, e.g., larger diameter towards cuff entry. However, it should be appreciated that the cuff may provide other suitable arrangements and/or protrusion configurations to facilitate retention with a respective tubular connector of the patient interface, PAP device, etc.

In an example, as shown in FIG. 7, each cuff includes a length d11 is about 5-7 mm, e.g., 6 mm.

Also, each cuff 20(1), 20(2) and the region 25 adjacent each cuff between the cuff and end zone Z2 includes no corrugations. It should be appreciated that the length of the non-corrugated region 25 may be adjusted, e.g., to change the flexibility and/or stretch characteristics.

Noise Mitigation

In an example, the conduit may include one or more structures to reduce noise in use. For example, the conduit may include insulation to reduce noise. For example, the insulation may be foam, fabric, foam and fabric, laminate, spacer fabric, and/or non-woven textile. The insulation may be provided to the inside or outside or combination of both on the tube. For example, the conduit may include an extra layer along its exterior surface to provide an insulating layer, or the conduit may include an extra layer along its interior surface to provide an insulating layer. Alternatively, an insulating layer may be molded into a thickness of the tube to insulate or reduce noise, e.g., a more rigid plastic may be insert molded into the tube to absorb noise.

Also, fewer or no corrugations may be provided along one or more zones of the conduit to reduce perceived noise, e.g., near the patient's ear. For example, see FIG. 13 with the larger corrugations near the patient's ear.

Materials

In an example, the conduit may be molded from polyethylene, polypropylene, EVA, or a blend of these materials.

In an example, the patient contacting side and the non-patient contacting side may be constructed from different materials, e.g., a co-extrusion. In another example, the patient contacting side and the non-patient contacting side may be constructed from the same material, e.g., a harder durometer and a softer durometer of the same material.

Manufacture

Another aspect of the present technology relates to a method of manufacturing an air delivery conduit with an asymmetrical cross-sectional profile, e.g., D-shaped cross-section as described above. In an example, the method (also referred to a blow or vacuum corrugated extrusion) includes an extrusion step followed by a blow-molding or vacuum forming step in one or more tools. In an example, a tool or mold creates a corrugation on one side of an extruded tube, while creating a flat profile on another side of the extruded tube.

For example, FIG. 15 shows an exemplary mold including an upper mold half M1 providing a side wall 80-1 structured to form the non-patient contacting side 40 of the tube and a lower mold half M2 providing a side wall 80-2 structured to form the patient contacting side 30 of the tube. In use, a small piece of plastic may be extruded into a space 85 defined between the mold halves, and then air is either blown through the plastic to push it outwards onto the walls of the mold (e.g., as shown in FIG. 15), or a vacuum is applied to suck the plastic onto the walls of the mold. The mold may be provided on a conveyor belt or "caterpillar" rotation so that a continuous piece of tube may be produced.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery conduit, comprising:
a tube including a plurality of corrugations,
wherein the corrugations vary along a length of the tube to change flexibility and/or stretch characteristics of the tube in one or more specific zones,
wherein the tube includes a perimeter that includes a relatively flat side along a portion of the perimeter that is substantially free from corrugations and a contoured side along a remaining portion of the perimeter that includes the corrugations, and
wherein an exterior of the contoured side is defined by a continuous convex surface that extends from one end of the remaining portion to an opposite end of the remaining portion.

2. An air delivery conduit according to claim 1, wherein the plurality of corrugations provide a series of parallel ridges and grooves, and each ridge extends generally perpendicular to a longitudinal axis of the tube.

3. An air delivery conduit according to claim 1, wherein the tube includes a generally D-shaped cross-section.

4. An air delivery conduit according to claim 1, wherein the relatively flat side includes a relatively flat interior surface and the contoured side includes a contoured interior surface, the relatively flat interior surface and the contoured interior surface establishing an air flow path adapted for air delivery.

5. An air delivery conduit according to claim 1, wherein the tube includes a generally D-shaped interior surface establishing an air flow path adapted for air delivery.

6. An air delivery conduit according to claim 1, wherein the relatively flat side is only provided to one side of tube along the perimeter.

7. An air delivery conduit according to claim 1, wherein the corrugations provide a series of parallel ridges and grooves, and the corrugations in a first zone include ridges with a smaller width and smaller spacing between adjacent ridges than corrugations in a second zone.

8. An air delivery conduit according to claim 1, wherein the contoured side includes a radius of curvature along its entire length.

9. An air delivery conduit according to claim 1, wherein the tube includes a major axis and a minor axis, and a ratio of the major axis to the minor axis is about 2-3.

10. An air delivery conduit according to claim 1, wherein the tube includes a hydraulic diameter of about 13-15.

11. An air delivery conduit, comprising:
a tube including a plurality of corrugations,
wherein corrugations in a first zone of the tube have a first corrugation characteristic and corrugations in a second zone of the tube have a second corrugation characteristic that is different than the first corrugation characteristic, and
wherein the corrugations are only provided along a selected portion of a perimeter of the tube such that the tube includes a corrugated portion along the selected portion of the perimeter and a non-corrugated portion along a remaining portion of the perimeter,
wherein the corrugated portion is provided along a curved side of the tube and the non-corrugated portion is provided along a relatively flat side of the tube, the curved side of the tube being defined by a continuous convex surface that extends from one end of the remaining portion to an opposite end of the remaining portion.

12. An air delivery conduit according to claim 11, wherein the first zone is provided to a central zone or section of the tube, and the second zone is provided to end zones or sections of the tube on opposing sides of the central zone.

13. An air delivery conduit according to claim 11, wherein the corrugations provide a series of parallel ridges and grooves.

14. An air delivery conduit according to claim 13, wherein corrugations in the second zone include ridges with a smaller width and smaller spacing between adjacent ridges than corrugations in the first zone.

15. An air delivery conduit according to claim 14, wherein corrugations in the second zone include ridges with a width of about 1.5 mm and a spacing of about 1.0 mm.

16. An air delivery conduit according to claim 14, wherein corrugations in the first zone include ridges with a width of about 2.5 mm and a spacing of about 1.5 mm.

17. An air delivery conduit according to claim 13, wherein each ridge extends generally perpendicular to a longitudinal axis of the tube.

18. An air delivery conduit according to claim 11, wherein the tube includes a generally D-shaped cross-section.

19. An air delivery conduit according to claim 11, wherein the tube includes a major axis and a minor axis.

20. An air delivery conduit according to claim 11, wherein the tube includes an inwardly facing surface adapted to contact a patient's face in use and the continuous convex surface is adapted to face away from a patient's face in use.

21. An air delivery conduit according to claim 20, wherein the relatively flat side provides the inwardly facing surface.

22. An air delivery conduit according to claim 20, wherein the inwardly facing surface is free from corrugations.

23. An air delivery conduit according to claim 11, wherein the tube includes a first end and a second end, and a cuff is provided to each of the first and second ends and adapted to engage a respective tubular connector.

24. An air delivery conduit according to claim 11, wherein the conduit is in the form of a non-heated tube.

25. An air delivery conduit according to claim 11, wherein the relatively flat side includes a relatively flat interior surface and the curved side includes a curved interior surface, the relatively flat interior surface and the curved interior surface establishing an air flow path adapted for air delivery.

26. An air delivery conduit according to claim 25, wherein the relatively flat side is only provided to one side of tube along the perimeter.

27. An air delivery conduit according to claim 11, wherein the tube includes a generally D-shaped interior surface establishing an air flow path adapted for air delivery.

28. An air delivery conduit, comprising:
a tube including a plurality of corrugations,
wherein the plurality of corrugations provide a series of parallel ridges and grooves, and each ridge extends generally perpendicular to a longitudinal axis of the tube,
wherein a portion of the tube that includes said corrugations is asymmetric about at least one axis,
wherein the portion includes a relatively flat side along a portion of a perimeter of the tube and a contoured side along a remaining portion of the perimeter,
wherein the corrugations are only provided along the contoured side of the tube, and
wherein the contoured side is defined by a continuous convex surface that extends from one end of the remaining portion to an opposite end of the remaining portion.

29. An air delivery conduit according to claim 28, wherein the portion includes a generally D-shaped cross-section.

30. An air delivery conduit according to claim 28, wherein the at least one axis is a major axis of the tube.

31. An air delivery conduit according to claim 28, wherein the relatively flat side includes a relatively flat interior surface and the contoured side includes a contoured interior surface, the relatively flat interior surface and the contoured interior surface establishing an air flow path adapted for air delivery.

32. An air delivery conduit according to claim 28, wherein the tube includes a generally D-shaped interior surface establishing an air flow path adapted for air delivery.

33. An air delivery conduit according to claim 28, wherein the relatively flat side is only provided to one side of tube along the perimeter.

34. A PAP system, comprising:
a PAP device structured to generate a supply of pressurized air;
a patient interface adapted to form a seal with the patient's face; and
at least one air delivery conduit according to claim 2 provided between the PAP device and the patient interface to deliver the supply of pressurized gas from the PAP device to the patient interface.

35. A PAP system according to claim 34, wherein the at least one air delivery conduit includes a pair of air delivery conduits.

36. A PAP system according to claim 35, wherein each conduit includes a first end engaged with a respective inlet of the patient interface and a second end engaged with a respective end of a manifold communicated with the PAP device.

37. A PAP system according to claim 35, wherein each conduit includes a first end engaged with a respective inlet of the patient interface and a second end engaged with a respective outlet of the PAP device.

38. A PAP system according to claim 34, wherein each air delivery conduit is adapted to extend from adjacent to or under the patient's nose, over the patient's cheeks, between the patient's eye and ear, and terminate at the crown of the patient's head.

39. A PAP system according to claim 38, wherein one or more zones of the tube include no corrugations or corrugations structured to reduce perceived noise.

40. A PAP system according to claim 39, wherein a zone of the tube adapted to extend adjacent the patient's ear in use includes no corrugations or corrugations structured to reduce perceived noise.

* * * * *

UNITED STATES PATENT AND TRADEMARK OFFICE
CERTIFICATE OF CORRECTION

| | | |
|---|---|---|
| PATENT NO. | : 8,978,648 B2 | Page 1 of 1 |
| APPLICATION NO. | : 13/064676 | |
| DATED | : March 17, 2015 | |
| INVENTOR(S) | : Formica et al. | |

It is certified that error appears in the above-identified patent and that said Letters Patent is hereby corrected as shown below:

In the Claims:

In claim 1, at column 9, line 36, "substantially free from corrugations and a contoured" should be corrected to ---free from corrugations and a contoured---.

Signed and Sealed this
Ninth Day of February, 2016

Michelle K. Lee
*Director of the United States Patent and Trademark Office*